United States Patent
Weber et al.

(10) Patent No.: US 6,423,209 B1
(45) Date of Patent: Jul. 23, 2002

(54) ACID GAS MEASURING SENSORS AND METHOD OF USING SAME

(75) Inventors: Martin Weber, Bonn; Christoph Braden, Köln; Serguei Tsapakh, Bonn, all of (DE)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/687,369

(22) Filed: Oct. 13, 2000

(51) Int. Cl.$^7$ .............................................. G01N 27/404
(52) U.S. Cl. ........................ 205/775; 204/291; 204/412; 204/415; 204/431; 205/779.5; 205/786.5
(58) Field of Search ................................ 204/415, 431, 204/432, 412, 291; 205/782, 782.5, 783, 778.5, 779.5, 775

(56) References Cited

U.S. PATENT DOCUMENTS

| | | | |
|---|---|---|---|
| 3,450,620 A | * | 6/1969 | Brewer |
| 3,470,071 A | * | 9/1969 | Vertes et al. |
| 3,622,487 A | * | 11/1971 | Chand |
| 3,795,589 A | | 3/1974 | Dahms |
| 4,474,648 A | * | 10/1984 | Tantram et al. |
| RE31,915 E | * | 6/1985 | Oswin et al. |
| 4,599,157 A | * | 7/1986 | Suzuki et al. |
| 5,228,974 A | * | 7/1993 | Kiesele et al. |
| 5,344,546 A | * | 9/1994 | Kiesele et al. |
| 5,395,507 A | * | 3/1995 | Aston et al. |

* cited by examiner

Primary Examiner—T. Tung
(74) Attorney, Agent, or Firm—Oliver A. Zitzmann; Margaret Chappuis; Steven J. Hultquist

(57) ABSTRACT

A electrochemical sensor for the detection of traces of HF and/or other acid gases in air, comprising a measuring electrode of an electrochemically active metal oxide powder, a reference electrode for fixing the potential of the measuring electrode close to the equilibrium potential of the oxidation/reduction system of $MeO_n/Me^{m+}$, and a counter electrode. The electrodes are in communicative contact with a hygroscopic electrolyte. The measured gas component changes the pH of the electrolyte, and thus the electrochemical equilibrium of the measuring electrode, to produce a measurable electrical current that is proportional to the concentration of the detected acid gas.

23 Claims, 2 Drawing Sheets

ACID GAS MEASURING SENSORS AND METHOD OF USING SAME

BACKGROUND OF THE INVENTION

1. Field of Invention

The present invention relates to electrochemical gas sensors, and more particularly, to electrochemical gas sensors for measuring acid gases.

2. Description of Related Art

Electrochemical sensors are widely used for measuring concentration of toxic gases. It is particularly important for an electrochemical sensor, used for gas detection, to possess high sensitivity, high accuracy, low (fast) response time and stability of characteristics in time. It is also essential that the sensor is selective, e.g., gases other than the one to be detected should cause small perturbations or preferably no signal at all.

In general, to be useful as an electrochemical sensor, a measuring and counter electrode combination must be capable of producing an electrical signal that is related to the concentration of the analyte. In addition to a measuring and counter electrode, an electrochemical sensor often includes a third electrode, commonly referred to as a reference electrode. A reference electrode, is used to maintain the working electrode at a known voltage or potential.

Generally, the electrodes of an electrochemical cell provide a surface at which an oxidation or a reduction reaction occurs involving the analyte. The electrochemical sensor produces an analytical signal via the generation of a current arising directly from the oxidation or reduction of the analyte gas (that is, the gas to be detected) at the measuring electrode. The measurable current arising from the cell reaction is directly proportional to the rate of reaction.

When measuring an electrochemically active gas, the gas makes contact with the measuring electrode and a process of oxidation or reduction of the gas molecules takes place, according to the type and character of the gas and the defined potential of the measuring electrode. Therefore, the measuring electrode acts as a catalyst for a RedOx process. Such a system is used for example to measure electrochemically active hydrogen sulfide. Hydrogen sulfide, upon contact with a catalytic platinum measuring electrode, is oxidized directly to sulfuric acid. Thus, the measuring electrode acts only as a catalyst for the oxidation process.

When the target gas is not electrochemically active, i.e., it cannot be oxidized or reduced, then other types of gas sensors must be employed. Suitable sensors for such non-electrochemically active gases include sensors that operate based on the principle of a precursor chemical reaction involving the participation of a target gas in the area of a three-phase boundary of the measuring electrode. The three-phase boundary is formed by the solid phase of the electrochemically active catalyst (electrocatalyst), the liquid phase of the electrolyte and the gas phase of the measuring gas. The product of the precursor chemical reaction is then electrochemically oxidized or reduced on the measuring electrode. This precursor chemical reaction principle has been applied using hydrogen fluoride (HF), a target gas that is not electrochemically active.

One of the known HF sensors, described in U.S. Pat. No. 3,795,58, incorporates the principle of a precursor chemical reaction involving the participation of hydrogen fluoride gas. Sensors of such type include measuring, reference and counter electrodes in contact with a water-based electrolyte. The electrolyte contains compounds that can be oxidized and/or reduced such as bromate/bromine-salts. Specifically, the acid properties of hydrogen fluoride are used to initiate the chemical reaction. As HF is adsorbed by an electrolyte, it forms ions $H_3O^+$ (Reaction 1), which take part in the following reaction (Reaction 2).

$$HF+H_2O=H_3O^++F- \quad (1)$$

$$5Br- +BrO_3- +6H^+=3Br_2 +3 H_2O \quad (2)$$

A pH shift in the electrolyte near the measuring electrode occurs in the presence of HF (Reaction 1). The second reaction (Reaction 2) proceeds with considerable rate only if the pH is close to or lower than 4. The generated bromine in the second reaction, cooperating with the electrocatalyst of the measuring electrode, is then reduced to a bromide ion as shown (Reaction 3).

$$Br_2+2e=2Br- \quad (3)$$

The reduction current is a measure of the concentration of the HF in the gas. Thus the electrochemical reaction is an indirect process where a precursor chemical (Reaction 2) takes place before an electrochemical reaction occurs.

The drawback of this type of HF sensor is an internal effect, which leads to a sensitivity decrease and an increase of response time during the life time of the sensor. On storing or during operation for several months, the electrolyte forms a small concentration of bromine due to a high amount of bromide ions already in the bulk electrolyte of the sensor. This in turn leads to a shift of the potential of the reference electrode as well as of the measuring electrode and thus to a lower sensitivity and slower response time in the presence of HF.

An additional reason for the slower response time is a shift of the pH in the electrolyte to higher values due to internal corrosion processes at the reference and counter electrodes. This is due to the high amount of bromate ions of the electrolyte. This bulk electrolyte pH increase leads to a delay in pH shift to the lower pH level necessary for starting reaction (Reaction 2) in the vicinity of the working electrode on exposure to HF gases.

It will be appreciated from the foregoing that there is a need in the acidic gas sensing field for an electrochemical sensor that overcomes the aforementioned problems of the prior art.

In particular, what is needed is a sensor that responds relatively quickly to changes of pH in the electrolyte, and eliminates the formation of unwanted by-products in the electrolyte that decrease sensitivity.

It is desirable, therefore, to develop an improved electrochemical gas sensor and electrodes for the detection of non-electrochemically active gases, which mitigate or substantially eliminate one or more of the above drawbacks.

SUMMARY OF THE INVENTION

In accordance with the present invention an improved electrochemical sensor is provided for measuring of non-electrochemically active gases. The improved electrochemical sensor has improved accuracy within its designed operating range, improved response speed, and remains stabilized over its designed operating lifetime.

Briefly and in general terms, the present invention provides an electrochemical cell and method for measuring the concentration of non-electrochemically active gases that form protons upon disassociation in an aqueous electrolyte, such as hydrogen fluoride (HF). On a fundamental level, the non-electrochemically active gaseous molecules are adsorbed on an electrolyte, dissociated into ions; these ions participate in a chemical reduction of reducible compounds located on a measuring electrode. This electrochemical cell advantageously comprises structural components and compounds that reduce the introduction of protons from sources other than the non-electrochemically active gases.

The electrochemical cell in one embodiment comprises a cell body including an electrolyte chamber for an aqueous electrolyte. The electrolyte chamber has a plurality of electrodes therein. These electrodes include an electrochemically active measuring electrode, a counter electrode and a reference electrode, with the respective electrodes being spaced apart from each other and mounted to the electrochemical cell body. The aqueous electrolyte electrically communicates the three electrodes by contacting all of them. An electrical circuit, connected to the electrodes, is constructed and arranged to quantify the current generated by the chemical reaction within the electrochemical cell.

The surface of the electrochemically active measuring electrode comprises a layer of an electrochemically active compound that is reducible in the presence of decreased pH levels in the aqueous electrolyte.

Preferably, the compound is a reducible metal oxide, and more preferably, a reducible metal oxide having a positive reduction potential that limits generation or consumption of protons from sources other than the proton-forming, non-electrochemically active gases. Most preferably, the reducible metal oxide is manganese dioxide or lead dioxide.

The surface of the counter electrode comprises a layer of an electrochemically active compound that is oxidizable, and preferably without the introduction of protons into the electrolyte. The aqueous electrolyte advantageously comprises a hygroscopic compound that is effective in preventing the evaporation of water from the electrolyte sensor, and preferably, the selected hygroscopic compound does not form protons in solution or in a pH buffer system.

The present invention in another aspect provides a method of using an electrochemical gas sensor comprising a measuring electrode, a counter electrode, a reference electrode and an aqueous electrolyte communicatively connecting the electrodes. In such sensor, the measuring electrode has an electrochemically active surface comprising a stable reducible metal oxide. The stable reducible metal oxide is reduced when the pH of the electrolyte is lowered due to the presence of increased proton concentration.

Such method comprises the steps of:
a) placing the electrochemical gas sensor in communicative connection with an environment containing a proton forming non-electrochemically active acid gas that is suitable to increase the proton concentration in the aqueous electrolyte to cause a chemical reduction of the reducible metal oxide on the measuring electrode; and
b) measuring the current flow between the measuring electrode and the counter electrode to obtain a measurement of the concentration of non-electrochemically active acid gas in the environment.

Other aspects, features and advantages of the invention will become more fully apparent from the ensuing description, drawings and appended claims.

DETAILED DESCRIPTION OF THE INVENTION AND PREFERRED EMBODIMENTS THEREOF

The present invention embodies various improvements in electrochemical gas sensors that are specific for non-electrochemically active acid gases.

Figure 1:
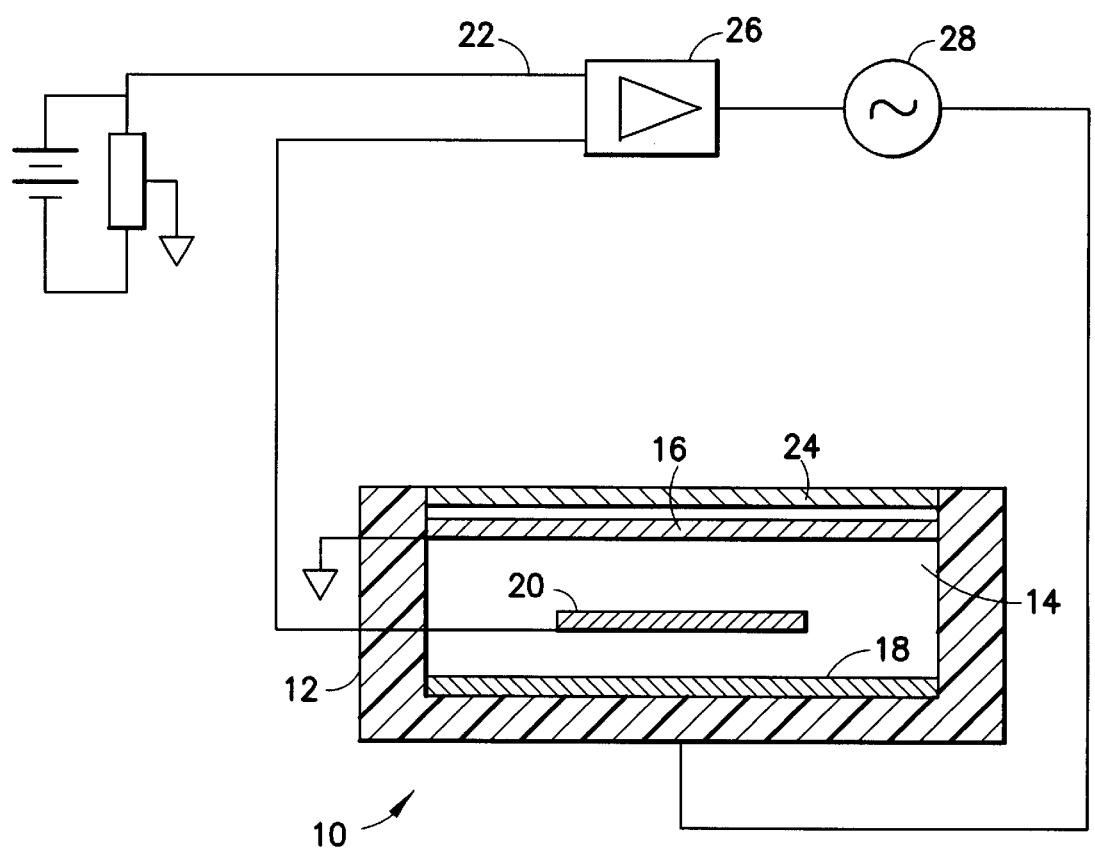
FIG. 1 shows a schematic view of a sensor according to one embodiment of the present invention.
Figure 2:
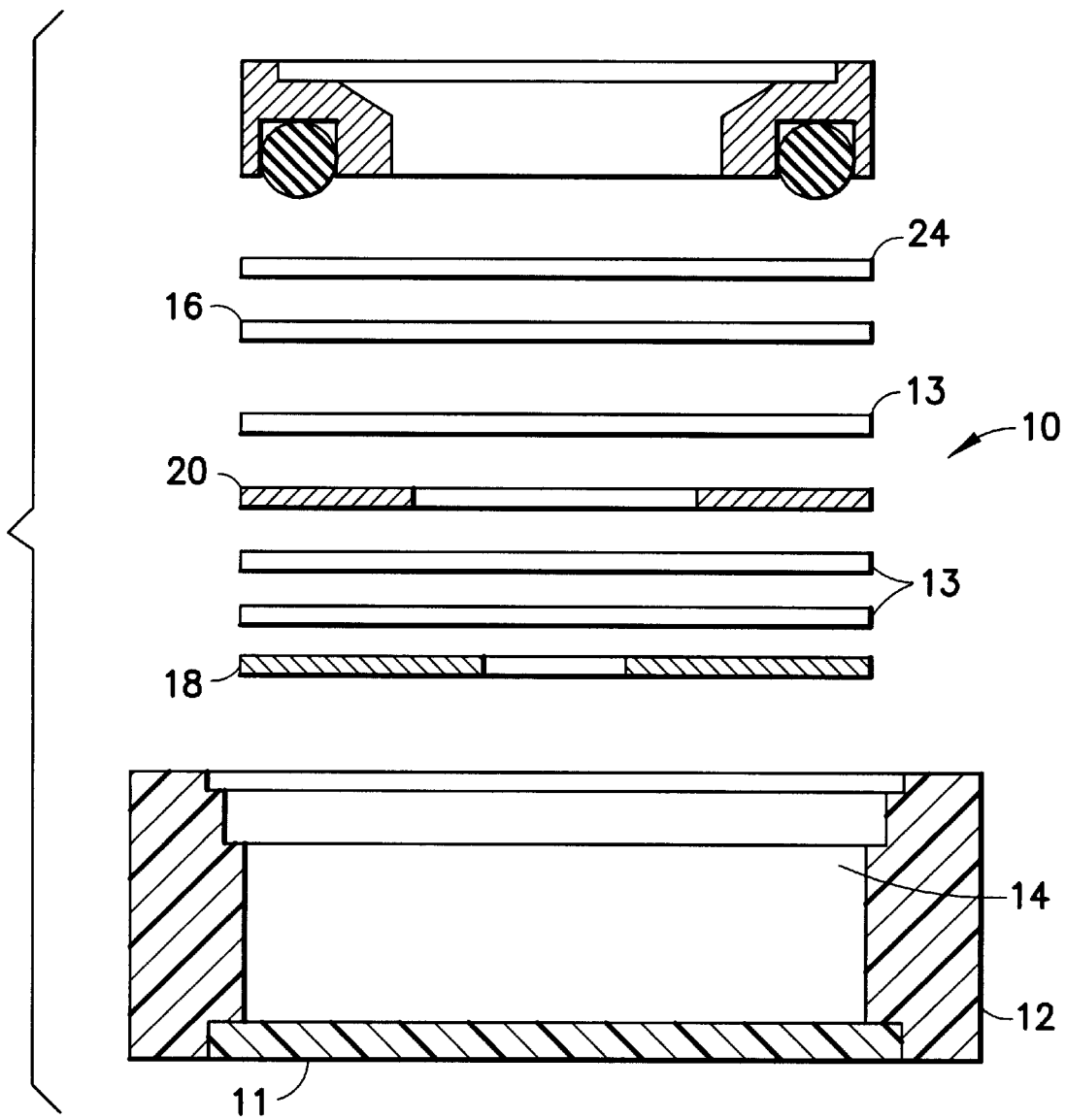
FIG. 2 is a fragmentary exploded view of the sensor illustrated in FIG. 1.

Referring to the drawings, as shown in FIGS. 1 and 2, the electrochemical gas sensor 10 includes a cell body 12 having an electrolyte chamber 14 defined by frame members of the cell body. A measuring electrode 16, a counter electrode 18 and a reference electrode 20 are substantially contained in the electrolyte chamber 14 and mounted to the frame members of the cell body 12.

An electrical circuit, generally designated 22, comprises a voltage source 26 that is arranged to provide a constant electrical potential to the measuring electrode 16 vs. reference electrode 20. The electric circuit is closed by counter electrode 18. An electrical measurement means, such as an ampmeter 28, monitors the current flow into the electrochemical gas sensor 10 and provides an output exhibiting a linear dependence to the concentration of the target gas.

The sensor as illustrated further comprises a diffusion barrier membrane 24 for diffusion of the gas to the measuring electrode. The diffusion barrier membrane controls transport of the target gas to the active measuring electrode while reducing the loss of electrolyte.

Cell body 12 provides means for supporting and positioning the other various elements of the sensor structure. The material of construction of the cell body, including frame members, may be any suitable material, e.g., an inert polymer that is resistant to the selected electrolyte.

Illustrative examples of such inert polymer include, without limitation, plastics such as polypropylene, polyvinylidene; acrylonitrile butadiene styrene (ABS); polyesters and the like.

Cell body 12 may be made as an integral single piece of plastic or from individual frame members that are sealed together to form a hermetically sealed cell. Preferably, as shown in FIG. 2, bottom frame member 11 is removable for entrance into the electrolyte chamber. After the electrolyte chamber has been filled, the bottom member may be hermetically sealed in place by ultrasonic welding or another conventional mode of sealing known in the art.

A suitable electrolyte fills the electrolyte chamber 14 defined by the frame members of the cell body. This electrolyte solution completely submerges the counter and reference electrodes 18 and 20 respectively, and preferably substantially covers the measuring electrode 16 to provide the aforementioned communicative connection between the measuring, counter and reference electrode.

The electrolyte may comprise any suitable aqueous based electrolyte that is compatible with the reagents employed. In one embodiment of the invention, the electrolyte may contain any salt that is hygroscopic and that does not form a pH buffer system. Preferably, the electrolyte comprises a hydrous solution of lithium chloride, LiCl, and more preferably, a mixture of lithium chloride with manganese(II) nitrate or manganese(II) sulfate. While the pH of the electrolyte may have any suitable value, a preferred pH operating condition is at a pH of approximately 4.

The measuring electrode 16 is disposed within the cell body 12 and is exposed to the target gas.

An important feature of the present invention, in view of the fact that the target gas is non-electrochemically active, is the addition of an electrochemically active compound in the measuring electrode 16. The measuring electrode may be impregnated with the electrochemically active compound or a surface layer of the electrochemically active compound may be applied thereon.

Any electrochemically active compound that is reduced in the presence of an acidic component, such as a proton $H_3O^+$, may be used for such purpose.

Preferably, the electrochemically active compound is a stable, reducible metal oxide including, for example, manganese dioxide (MnO2) or lead dioxide ($PbO_2$). More preferably, manganese dioxide $MnO_2$ is used because of its unique properties stemming from the fact that the oxidation potential of the reaction (Reaction 4):

$$MnO_2 + 4H^+ + 2e = Mn^{2+} + 2H_2O \quad Eo=1.21\ V \qquad (4)$$

is almost equal to that of the reaction (Reaction 5):

$$O_2 + 4H^+ + 4e = 2H_2O \quad Eo=1.23\ V \qquad (5)$$

This means that the RedOx system $MnO_2/Mn^{2+}$ in hydrous electrolyte is stable. $MnO_2$ neither tends to oxidize oxygen of water to elementary oxygen, as all the systems with higher potential would do, nor does $MnO_2$ reduce dissolved oxygen to water, as do the systems with lower potential. As a result there is no additional and unwanted $H_3O^+$ generated or consumed and the electrolyte pH remains stable during long-term storage or during sensor operation.

It is also possible to use powder of lead dioxide $PbO_2$ as an electrochemically active material of the working electrode. The current-forming reaction (Reaction 6) in this case is:

$$PbO_2 + 4H^+ + 2e = Pb^{2+} + 2H_2O \quad Eo=1.46\ V \qquad (6)$$

The behavior of this system is close to that of the manganese dioxide system. The potential of the lead dioxide/lead ions is higher than the oxygen potential and could otherwise cause some water decomposition, but the kinetics of this process are very slow, providing high stability of lead dioxide in water solutions.

The measuring electrode 16 is prepared by mixing powders of inert, electrically conductive materials, such as carbon, with the electrochemically active compound. Preferably, the electrochemically active compound is added to the mixture in an amount ranging from about 10% to about 80% by weight, and more preferably from about 25% to about 60% by weight, based on the total weight of the mixture.

Preferably, the measuring electrode is fabricated from a mixture of the reducible metal oxide and graphite, and more preferably, a mixture of $MnO_2$ and graphite applied to a substrate comprising a water-resistant polymeric material, e.g., a PTFE film. While graphite powder or felt is preferred as a conductive component of the mixture, other materials with good electrical conductivity can be used, e.g. powders of gold, iridium and ruthenium.

The graphite mixture may be applied to a polytetrafluoroethylene (PTFE) film substrate by conventional procedures. Typically, the mixture is formed into an aqueous slurry containing a sufficient amount of the reducible metal oxide to provide a surface layer containing about 5 mg/cm² to about 15 mg/cm² of the metal oxide on the measuring electrode. The graphite mixture is then placed onto the electrode substrate with a spatula, roller or any other technique, which will apply it uniformly to the surface of the substrate.

Typically, the graphite mixture layer will be about 0.1 mm to about 0.5 mm in thickness, with a preferred range of about 0.1 mm to about 0.2 mm.

In a preferred embodiment, the aqueous slurry containing the graphite and a reducible metal oxide is further mixed with a hydrophobic material such as PTFE. The slurry is mixed thoroughly to ensure homogeneity and then applied to the electrode surface as described above. Typically, the PTFE is added in an amount ranging from about 10% to about 75% by weight of the graphite/metal oxide mixture and more preferably from about 20% to about 50% by weight.

Once the graphite mixture has been placed on the PTFE substrate, the structure is placed in an oven and sinter-bonded. Typically, this is done at temperatures of about 150° C. to about 330° C. preferably between 170° C. and 180° C. for about 1 minutes to about 13 hours. The sintering process causes the PTFE in the graphite mixture to bond or fuse with the PTFE of the film substrate, to thereby securely bond the graphite mixture to the film substrate.

The PTFE membrane of the measuring electrode is important because it serves not only as a barrier for the electrolyte, but also as a diffusion barrier for the target gas.

The reducible metal oxide, acting as a catalytic surface, is in contact with the electrolyte and is partly penetrated by the target gas so that a three-phase boundary is present. This three-phase boundary consists of electrolyte, catalytic surface and the target gas. It is at this boundary that the electrochemical reaction occurs to provide a measurable signal. The current-forming reaction (Reaction 4), is very sensitive to pH change of the electrolyte. As a result, the acid gas, diffusing through the PTFE membrane, causes an immediate increase of $H_3O^+$ concentration (Reaction 1) so that the electrochemical reduction of manganese (IV) to manganese (II) can occur.

While in the presence of acid gases, such as HF, an electrochemical reduction of manganese dioxide or lead dioxide takes place on the measuring electrode 16, and as such, an oxidation reaction is promoted on the counter electrode 18. To maintain the sensitivity of the present sensor, any oxidation reaction that generates protons, should be avoided, e.g., processes of water (Reaction 7) or $Mn^{2+}$ (Reaction 8) oxidation:

$$H_2O = 2\ H^+ + \tfrac{1}{2}\ O_2 + 2e- \qquad (7)$$

$$Mn^{2+} H_2O = MnO_2 + 4\ H^+ + 2\ e^- \qquad (8)$$

Proton generation should be avoided to prevent diffusion of protons to the counter electrode 18 through the bulk of the electrolyte to the measuring electrode 16 since this will generate a current and lead to a constant rise of zero current.

In order to avoid this phenomenon, the counter electrode 18 can be fabricated from a substance that is capable of oxidation with no generation of protons, such as silver, e.g., in the form of a net, wire or powder supported on a substrate. The oxidation reaction, as shown below (Reaction 9), in the presence of the aqueous electrolyte, proceeds with no formation of protons.

$$Ag + LiCl = AgCl + Li^+ + e^- \qquad (9)$$

It also is to be noted that in the presence of the lithium chloride electrolyte solution, passivation of silver proceeds in a natural way by formation of the dense layer of AgCl. Passivation provides a protective cover of AgCl on the surface of the silver, thereby reducing corrosion of the silver electrode. Silver corrosion is desirably avoided because corrosion, due to oxygen dissolved in solution, causes an increase in the pH of the electrolyte solution, with a concomitant increase in response time.

The gas sensor of the present invention functions on the amperometric principle, i.e. the measured current is proportional to the target gas concentration in the ambient air. The reference electrode 20 serves as this electrical reference point, which when combined with an external electronic potentiostatic circuit maintains a constant working electrode potential. In this case the reference electrode fixes the potential of the measuring electrode close to the equilibrium potential of the oxidation/reduction system $MeO_n/Me^{m+}$, wherein 2and m represent oxidation forms of the metal in the initial material of the working electrode (2n) and in the product of the reaction (m).

Reference electrode 18 may be fabricated from any electrically conductive material and in any configuration, such as an overall ring or annular shape with a central aperture. Preferably, platinum black is used as an active part of the reference electrode and covers the surface of a porous film, e.g., made of a material such as polytetrafluoroethylene. Platinum black is preferably selected because it has a potential that is equal to the optimal potential for function of the above-described measuring electrode.

In this case, the potential of the measuring electrode is maintained equal to that of the reference electrode, i.e., no bias potential is applied between these two electrodes. While platinum black is a preferred catalyst material, various other materials can also be used, e.g., a mixture of $MnO_2$ and graphite powder.

Fabrication of the reference electrode employs a construction similar to the measuring electrode. Preferably, reference electrode 20 comprises a tape support, e.g., of PTFE material. A catalyst, preferably of platinum black, is formed as a wet mixture with a tetrafluoroethylene material. This mixture is then applied to the porous tape support and allowed to dry. The support layer and the catalyst layer then are pressed together and sintered to form an intimate bond between the two.

The potential between measuring electrode 16 and reference electrode 20 is kept constant by a potentiostat 26 and when the target gas changes the pH of the electrolyte, a measurable electrical characteristic, such as current flowing between the electrodes, is produced which is proportional to the concentration of the target acid gas.

Thus, when the environment being monitored contains a toxic acid gas for which the measuring electrode and electrolyte have been chosen to produce a change in the electrical characteristics of the measuring electrode (with respect to the counter electrode in the presence of the acid gas), an electrical measurement means detects the change of electrical characteristic. The electrical characteristic may optionally provide a display of contamination concentration, may trigger a warning or control device, or may be stored in a storage or memory device for later comparison and review. In the preferred practice of the present invention, the electrical characteristic is the change in current flowing between the electrodes.

The electrochemical sensor in the illustrated embodiment further comprises a diffusion barrier 24 comprising a porous conventional polytetrafluoroethylene membrane. The membrane controls transport of the target gases to the electrochemically active compounds of the measuring electrode while preventing the loss of electrolyte.

The physical construction of the electrochemical sensor 10 according to the previously described embodiment of the present invention will now be discussed with additional reference to FIG. 2. Sensor 10 includes a cell body 12 with an internal cavity or electrolyte chamber 14 adapted for filing with an electrolyte. As will be seen in the illustrated embodiment, the internal cavity of the cell may be sealed at the top by an electrode assembly generally indicated at 30. Entrance to the cavity of cell body may be gained by removing bottom cover 11, which is hermetically sealed to cell body 10 after the electrolyte has been filled. Ultrasonic welding or other conventional mode of sealing is suitably employed.

The electrodes of the electrode assembly 30 are co-axially stacked within the electrolyte chamber and communicatively connected through the electrolyte.

The invention is further elucidated by the following non-limiting examples.

EXAMPLE 1

A series of sensors was produced according to the invention with the measuring electrode made of porous Teflong membrane covered by a mixture of 25% wt. manganese dioxide and 75% wt. graphite powder with Teflon® (E.I. DuPont de Nemours and Company, Wilmington, Del.) polytetrafluoroethylene suspension as a binder. A reference electrode was fabricated of platinum black on a porous membrane. The counter electrode was silver wire. The central gas aperture of the upper cover was constructed with a central diameter of 7 mm.

The electrolyte was a 320 g/l water solution of LiCl. Approximately 0.4 ml of the electrolyte was added to the electrolyte chamber of the sensor, leaving a portion of the chamber unfilled to accommodate any water vapor that may diffuse into the sensor, should the hydrous electrolyte become diluted by an elevated humidity level in the ambient atmosphere.

After filling with the electrolyte, the bottom of cell was hermetically sealed with ultrasonic welding of the bottom cover. The potential difference between the measuring and reference electrodes was adjusted to zero with zero current measuring less than 15 nA over a waiting period of several minutes.

The sensors were tested for HF at concentration 6–8ppm. All of them had sensitivity 800 ±50 nA/ppm, with a response time $t_{50}$ in the range of 4–11 seconds. It was also noted that the values of about 4 seconds were characteristic for the sensors with silver wire counter electrodes, and 7–11 seconds for the case of silver net counter electrodes.

As soon as the sensors were exposed to fresh air, the current fell to a low value of 2–15 nA within 20 seconds.

Exposure to HF was repeated several times, resulting in near-identical values.

EXAMPLE 2

The sensors according to Example 1 were held at 45° C. in hermetically closed vessels for 300 hours. After the test no significant loss of sensitivity and no increase of response time was noted. Other sensors from the same pilot plant production lot were crash-tested at 100% relative humidity and 52° C. for 160 hours. Sensitivities of the sensors after this test fell from 800 50 nA/ppm to 480–640 nA/ppm and the response time $t_5$ increased from about 4–9 seconds to about 10–32 seconds.

It was noted that for the sensors with silver wire counter electrodes, the response time $t_{50}$ value reached only 10–11 seconds, while for the case of silver net counter electrodes, the response time $t_{50}$ increased to 19–32 seconds.

In approximately two months after the above-described initial tests, the sensitivities of the sensors with the wire counter electrode returned essentially to the initial values. In contrast, the sensors with silver net counter electrodes did not return to the initial values, but instead, both sensitivity and too values remained at the same levels as measured immediately after the crash test.

EXAMPLE 3

Sensors constructed according to Example 1 were exposed to an environment containing about 8 ppm HF for a 90 minute period. No decrease of the signal occurred during this time.

EXAMPLE 4

A sensor was produced with the measuring electrode made of porous Teflon® membrane covered by a mixture comprising 25% wt. manganese dioxide(0.19 grams) and 75% wt. graphite powder and a Teflon® suspension as a binder. A reference electrode was fabricated from platinum black on a porous membrane. The counter electrode was silver wire. The electrolyte was a 320 g/l water solution of LiCl. The manganese (IV)- material of the measuring electrode was consumed. The calculations according to the reaction (Reaction 4). showed that at 100% consumption, the capacity was sufficient to produce a signal of about 150 ppm-h, corresponding to an operating time of 50 hours at a concentration of 3 ppm HF in the measured environment (TLV value).

EXAMPLE 5

Sensors were constructed according to Example 1 and were tested for cross-sensitivity to other gases. The results are presented in the Table 1 below.

TABLE 1

| Gas | Concentration, ppm | Reading, ppm |
|---|---|---|
| Chlorine | 1 | 0.4 |
| Hydrochloric acid | 5 | 3.5 |
| Carbon monoxide | 1000 | 0 |
| Hydrogen | 10000 | 0 |
| Carbon dioxide | 5000 | 0 |

Results indicate that when sensors fabricated in accordance with the present invention are used for testing of toxic hydrogen fluoride gas in ambient air conditions, other gaseous component present in the air samples, such as carbon dioxide, hydrogen and carbon monoxide, do not reduce the accuracy of the testing results.

EXAMPLE 6

A series of sensors was produced according to the present invention with the measuring electrode made of porous Teflon® membrane covered by a mixture from the following composition: 80% mass manganese dioxide-20% mass graphite powder, 50% mass manganese dioxide-50% mass graphite powder, 10% mass manganese dioxide-90% mass graphite powder, and a Teflon® suspension as a binder.

A reference electrode was fabricated of platinum black presented on a porous membrane. The counter electrode was silver wire. The electrolyte was a 320 g/l water solution of LiCl.

The sensors were tested for HF at concentration level of 6–8ppm. The sensitivity values of the sensors for all three ratios of manganese oxide/graphite powder were in the range 800 ±50 nA/ppm, with a $t_{50}$ equal to 3–5 seconds.

While the invention has been described herein with reference to illustrative aspects, features and embodiments, it will be appreciated that the utility and scope of the invention are not thus limited, but rather that the invention is susceptible of being embodied in numerous other forms, configurations and arrangements, and practiced with numerous other techniques, methods and approaches. The invention therefore is intended to be broadly interpreted and construed, in respect of the claims hereinafter set forth.

What is claimed is:

1. An electrochemical gas sensor for measuring a proton-forming, non-electrochemically active gas, said sensor comprising:
    a) an electrolyte chamber containing an aqueous electrolyte;
    b) a measuring electrode comprising a reducible metal oxide selected from the group consisting of manganese dioxide and lead dioxide that reduces to a lower oxidation sate by an electrochernical reduction process in the presence of increased protons in the aqueous electrolyte introduced by the proton forming non-electrochemically active gas said measuring electrode being exposed to be ambient,
    c) a reference electrode in contact with the electrolyte and communicating therethrough with the measuring electrode; and
    d) a counter electrode in contact with the electrolyte and communicating therethrough with the measuring electrode.

2. The electrochemical gas sensor according to claim 1, wherein the measuring electrode further comprises a support layer and has disposed thereon a powder mixture of the reducible metal oxide and a conductive substance effective to conduct an electrical current.

3. The electrochemical sensor according to claim 2, wherein the concentration of the reducible metal oxide in the powder mixture is from about 10% to about 80% by weight, based on the total weight of the powder mixture.

4. The electrochemical sensor according to claim 2, wherein the support layer of the measuring electrode comprises polytetrafluoroethylene.

5. The electrochemical sensor according to claim 2, wherein the powder mixture is bonded to the support layer.

6. The electrochemical sensor according to claim 1, wherein the reducible metal oxide has a positive standard reduction potential that limits generation or consumption of protons from sources other than the proton-forming non-electrochemically active gases.

7. The electrochemical sensor according to claim 1, wherein the measuring electrode further comprises a conductive substance effective to conduct electric current.

8. The electrochemical sensor according to claim 7, wherein the conductive substance comprises a material selected from the group consisting of gold powder, graphite powder, graphite felt, and mixtures thereof.

9. The electrochemical sensor according to claim 1, wherein the aqueous electrolyte comprises a hygroscopic and pH-neutral salt.

10. The electrochemical sensor according to claim 1, wherein the reference electrode comprises a mixture of platinum powder and a hydrophobic polymeric binder.

11. The electrochemical sensor according to claim 1, wherein the reference electrode is identical to the measuring electrode.

12. The electrochemical sensor according to claim 1, wherein the counter electrode contains a substance effective to be oxidized without the formation of protons in the electrolyte.

13. The electrochemical sensor according to claim 12, wherein the counter electrode comprises an oxidizable structure selected from the group consisting of silver net, silver powder, and silver wire.

14. A method of using an electrochemical gas sensor comprising a measuring electrode exposed to the ambient, a counter electrode, and an aqueous electrolyte communicatively connecting the electrodes, the measuring electrode having an electrochemically active surface comprising a stable reducible metal oxide selected from the group consisting of manganese dioxide and lead dioxide, and that is reduced when the pH of the electrolyte is lowered in the presence of increased proton concentration, said method comprising the steps of:

a) placing the electrochemical gas sensor in communicative connection with an environment, including a proton forming non-electrochemically active acid gas suitable to increase the proton concentration in the aqueous electrolyte and cause a chemical reduction of the reducible metal oxide of the measuring electrode; and b) measuring the current flow between the measuring electrode and the counter electrode to obtain a measurement of the concentration of non-electrochemically active acid gas in the environment.

15. The method according to claim 14, wherein the measuring electrode further comprises a support layer having disposed thereon a powder mixture of the reducible metal oxide and a conductive substance effective to conduct an electrical current.

16. The method according to claim 15, further comprising a reference electrode.

17. The method according to claim 15, wherein the conductive substance comprises a material selected from the group consisting of gold powder, graphite powder, graphite felt, and mixtures thereof.

18. The method according to claim 14, wherein the reducible metal oxide has a positive standard reduction potential that limits generation or consumption of protons from sources other than the proton-forming non-electrochemically active gas.

19. The method according to claim 14, wherein the reducible metal oxide of the measuring electrode comprises lead dioxide.

20. The method according to claim 14, wherein the aqueous electrolyte comprises a hygroscopic and pH-neutral salt.

21. The method according to claim 14, wherein the reference electrode comprises a mixture of platinum powder and a hydrophobic polymeric binder.

22. The method according to claim 14, wherein the counter electrode comprises a substance effective to be oxidized without the formation of protons in the electrolyte.

23. The method according to claim 14, wherein the counter electrode comprises an oxidizable structure selected from the group consisting of silver net, silver powder, and silver wire.

\* \* \* \* \*